United States Patent [19]

Berg

[11] Patent Number: 5,106,459
[45] Date of Patent: Apr. 21, 1992

[54] SEPARATION OF P-MENTHANE FROM P-CYMENE BY EXTRACTIVE DISTILLATION

[75] Inventor: Lloyd Berg, 1314 South Third Ave., Bozeman, Mont. 59715

[73] Assignee: Lloyd Berg, Bozeman, Mont.

[21] Appl. No.: 627,252

[22] Filed: Dec. 14, 1990

[51] Int. Cl.$^5$ .............................. B01D 3/40; C07C 7/08
[52] U.S. Cl. ........................................ 203/51; 203/56; 203/60; 203/62; 203/63; 203/64; 585/806; 585/864; 585/866
[58] Field of Search .................. 203/60, 62, 63, 64, 203/51, 56; 585/800, 803, 804, 806, 833, 864, 866

[56] References Cited

U.S. PATENT DOCUMENTS

| | | | |
|---|---|---|---|
| 2,952,717 | 9/1960 | Fleck et al. | 585/864 |
| 3,288,688 | 11/1966 | Kane | 585/803 |
| 3,366,568 | 1/1968 | Eisenlohr et al. | 585/864 |
| 3,530,195 | 9/1970 | Amir | 585/806 |
| 4,128,594 | 12/1978 | Westernacher | 585/806 |
| 4,514,262 | 4/1985 | Berg | 585/864 |

Primary Examiner—Wilbur Bascomb, Jr.

[57] ABSTRACT p-Cymene and p-menthane are difficult to separate one from another by conventional distillation or rectification because of the close proximity of their boiling points. p-Cymene and p-menthane can be readily separated one from another by using azeotropic or extractive distillation. Typical examples of effective agents, for azeotropic distillation: diethyelene glycol ethyl ether, 1-pentanol and isobutanol; for extractive distillation: butyl benzoate, undecyl alcohol and methyl benzoate.

2 Claims, No Drawings 6,106,459

SEPARATION OF P-MENTHANE FROM P-CYMENE BY EXTRACTIVE DISTILLATION

FIELD OF THE INVENTION

This invention relates to a method for separating p-menthane from p-cymene using certain organic compounds as the agent in azeotropic or extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

p-Menthane (1-methyl-4-isopropyl cyclohexane), B.P.=171° C. and p-cymene (1-methyl-4isopropyl benzene), B.P.=175° C. have a relative volatility of only 1.19 and are difficult to separate by rectification. Extractive distillation would be an attractive method of effecting the separation of p-menthane from p-cymene if agents can be found that (1) will enhance the relative volatility between p-menthane and p-cymene and (2) are easy to recover, that is, form no azeotrope with p-methane or p-cymene and boil sufficiently above these to make separation by rectification possible with only a few theoretical plates. Azeotropic distillation would also be an attractive method of separating these two if agents can be found that will enhance the relative volatility sufficiently. p-Cymene can be made by the catalytic dehydrogenation of the saturated ring in p-menthane (1-methyl-4-isopropyl cyclohexane) to convert it into p-cymene (1-methyl-4- isopropyl benzene). Since the conversion is not complete and these two compounds boil only four Celcius degrees apart, separation by distillation is difficult.

The advantage of using azeotropic or extractive distillation in this separation can be seen from the data shown in Table 1 below.

TABLE 1

Theoretical And Actual Plates Required vs. Relative Volatility For p-Menthane - p-Cymene Separation

| Relative Volatility | Theoretical Plates Required At Total Reflux, 99% Purity | Actual Plates Required, 75% Eff. |
|---|---|---|
| 1.19 | 53 | 71 |
| 1.5 | 23 | 31 |
| 2.0 | 13 | 17 |
| 2.5 | 10 | 13 |
| 3.0 | 8 | 11 |

The relative volatility of p-menthane to p-cymene is 1.19 and thus require 53 theoretical plates for separation by conventional rectification at total reflux. Plates possessing an efficiency of 75% are commonly employed and thus about 71 actual plates are required, clearly a difficult separation. Several of the agents that I have discovered yield a relative volatility of 2.5 or higher which would reduce the plate requirement to only 13.

Extractive distillation typically requires the addition of an equal amount to twice as much extractive agent as the p-menthane - p-cymene on each plate of the rectification column. The extractive agent should be heated to about the same temperature as the plate into which it is introduced Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable also that the extractive agent be miscible with the p-cymene otherwise it will form a two-phase azeotrope with the p-cymene in the recovery column and some other method of separation will have to be employed.

OBJECTIVE OF THE INVENTION

The objects of this invention are to provide a process or method of azeotropic or extractive distillation that will enhance the relative volatility of p-menthane to p-cymene in their separation in a rectification column. It is a further object of this invention to identify organic compounds that are stable, can be separated from p-cymene by rectification with relatively few plates and can be recycled to the extractive distillation column with little decomposition.

SUMMARY OF THE INVENTION

The objects of the invention are provided by a process for the separation of p-menthane from p-cymene which entails the use of certain organic compounds as the agent in azeotropic or extractive distillation.

DETAILED DESCRIPTION OF THE INVENTION

I have discovered that certain organic compounds will effectively increase the relative volatility between p-menthane and p-cymene and permit the separation of p-menthane from p-cymene by rectification when employed as the agent in azeotropic or extractive distillation. Table 2 lists the agents that I have found to be effective as azeotrope formers with p-methane and remove p-menthane as the overhead product from p-cymene. The data in Tables 2, 3, 4 and 5 were obtained in a vapor-liquid equilibrium still. In every case, the starting material was a mixture of p-menthane and p-cymene in the ratio of about 40% p-menthane, 60% p-cymene. The relative volatilities are listed for each of the agents. The compounds which are effective azeotrope formers to remove p-menthane as overhead from p-cymene are benzyl alcohol, nitrobenzene 3-methyl-1-butanol, 2-methyl-1-butanol, 3-pentanol, isobutanol, 2-butanol, benzonitrile, diethylene glycol ethyl ether and diethylene glycol diethyl ether.

Table 3 lists the agents that I have found to be effective as azeotrope formers with p-cymene and remove p-cymene as the overhead product from p-menthane. The compounds which are effective azeotrope formers to remove p-cymene as overhead from p-menthane are 2-octanol, 1-penthanol, alpha-methyl benzyl alcohol and dipropylene glycol methyl ether.

Table 4 lists the compounds that I have found to be effective extractive distillation agents to remove p-menthane as overhead product from p-cymene. The compounds which are effective are methyl benzoate, butyl benzoate, methyl salicylate, ethyl benzoate, 2-hydroxyacetophenone, acetophenone, ethylene glycol diacetate, benzyl acetate, benzyl benzoate, diethyl maleate, diethylene glycol butyl ether, diethylene glycol hexyl ether, tripropylene methyl ether, benzyl ether Table 5 lists the compounds that I have found to be effective extractive distillation agents to recover p-cymene as overhead product from p-menthane. The compounds which are effective are glycerol triacetate, isobutyl heptyl ketone 2-undecanone, undecyl alcohol, isodecyl alcohol and cyclododecanol.

TABLE 2

Effective Azeotropic Agents For Separating p-Menthane From p-Cymene. p-Menthane In The Overhead

| Compounds | Relative Volatility |
|---|---|
| None | 1.19 |
| Nitrobenzene | 1.3 |
| 3-Methyl-1-butanol | 1.4 |
| 2-Methyl-1-butanol | 1.5 |
| 3-Pentanol | 5.9 |
| Isobutanol | 2.4 |
| 2-Butanol | 9.1 |
| Benzyl alcohol | 1.8 |
| Benzonitrile | 2.8 |
| Diethylene glycol ethyl ether | 3.8 |
| Diethylene glycol diethyl ether | 1.5 |

TABLE 3

Effective Azeotropic Agents For Separating p-Menthane From p-Cymene, p-Cymene In The Overhead

| Compounds | Relative Volatility |
|---|---|
| 2-Octanol | 1.3 |

TABLE 3-continued

Effective Azeotropic Agents For Separating p-Menthane From p-Cymene. p-Cymene In The Overhead

| Compounds | Relative Volatility |
|---|---|
| 1-Pentanol | 2.7 |
| alpha-Methyl benzyl alcohol | 1.6 |
| Dipropylene glycol methyl ether | 2.1 |

TABLE 4

Effective Extractive Distillation Agents For Separating p-Menthane From p-Cymene. p-Menthane In The Overhead

| Compounds | Relative Volatility |
|---|---|
| Methyl benzoate | 1.8 |
| Butyl benzoate | 2.5 |
| Methyl salicylate | 1.4 |
| Ethyl benzoate | 2.3 |
| 2-Hydroxy acetophenone | 2.4 |
| Acetophenone | 1.8 |
| Ethylene glycol diacetate | 1.5 |
| Benzyl acetate | 1.5 |
| Benzyl benzoate | 1.4 |
| Diethyl maleate | 2.1 |
| Diethylene glycol butyl ether | 1.4 |
| Diethylene glycol hexyl ether | 1.5 |
| Tripropylene glycol methyl ether | 2.7 |
| Benzyl ether | 1.3 |
| Nonyl alcohol | 1.8 |

TABLE 5

Effective Extractive Distillation Agents For Separating p-Menthane From p-Cymene, p-Cymene In The Overhead

| Compounds | Relative Volatility |
|---|---|
| Glycerol triacetate | 1.5 |
| Isobutyl heptyl ketone | 1.4 |
| 2-Undecanone | 1.5 |
| Undecyl alcohol | 2.9 |
| Isodecyl alcohol | 1.9 |
| Cyclododecanol | 3.9 |

Table 6 lists a number of compounds which might have been expected to act favorably in the separation of p-menthane from p-cymene but which failed to yield an effective relative volatility.

TABLE 6

Ineffective Agents For Separating p-Menthane From p-Cymene

| | |
|---|---|
| Dihexyl phthalate | 2-Methyl pyrrolidone |
| Ethylene carbonate | Propylene carbonate |
| Ethyl salicylate | Dioctyl sebacate |
| Diethyl malonate | n-Decanol |
| Hexyl alcohol | n-Butanol |
| 2-Methyl pentanol | 2-Ethyl-1-hexanol |
| 2-Ethyl butanol | |

Two of the agents whose relative volatilities had been determined in the vapor-liquid equilibrium still were then evaluated in a glass perforated plate rectification column possessing 7.3 theoretical plates and the results listed in Table 7.

TABLE 7

Data From Runs Made In Rectification Column - p-Menthane From p-Cymene

| Agent | Mode | Column | Time hrs. | Weight % p-Menthane | Weight % p-Cymene | Relative Volatility |
|---|---|---|---|---|---|---|
| Isobutanol | Azeotropic | Overhead | 2 | 99.9 | 0.1 | 2.3 |
| | | Bottoms | | 68.5 | 31.5 | |
| Isobutanol | Azeotropic | Overhead | 4 | 99.9 | 0.1 | 2.4 |
| | | Bottoms | | 58.5 | 41.5 | |
| Methyl benzoate | Extractive | Overhead | 1 | 91 | 9 | 1.64 |

TABLE 7-continued

Data From Runs Made In Rectification Column - p-Menthane From p-Cymene

| Agent | Mode | Column | Time hrs. | Weight % p-Menthane | Weight % p-Cymene | Relative Volatility |
|-------|------|--------|-----------|---------------------|-------------------|---------------------|
|       |      | Bottoms |          | 21.2                | 78.8              |                     |

Isobutanol was evaluated in the azeotropic distillation mode and gave relative volatilities of 2.3 and 2.4. Methyl benzoate was evaluated in the extractive distillation mode and yielded a relative volatility of 1.64.

THE USEFULNESS OF THE INVENTION

The usefulness or utility of this invention can be demonstrated by referring to the data presented in Tables 2 to 7. All of the successful agents show that p-menthane and p-cymene can be separated one from the other by means of azeotropic or extractive distillation in a rectification column and that the ease of separation as measured by relative volatility is considerable.

WORKING EXAMPLES

1. Forty grams of a p-methane - p-cymene mixture and 20 grams of diethylene glycol ethyl ether were charged to a vapor-liquid equilibrium still and refluxed for five hours. Analysis indicated a vapor composition of 53.7% p-methane, 46.3% p-cymene in the azeotrope; a liquid composition of 23.3% p-menthane, 76.7% p-cymene which is a relative volatility of 3.8.

2. Forty grams of a p-methane - p-cymene mixture and 20 grams of 1-pentanol were charged to the vapor-liquid equilibrium still and refluxed for four hours. Analysis indicated a vapor composition of 16.8% p-menthane, 83.2% p-cymene in the azeotrope; a liquid composition of 35.2% p-menthane, 65.8% p-cymene which is a relative volatility of p-cymene to p-menthane of 2.7.

3. Forty grams of a p-methane - p-cymene mixture and 20 grams of butyl benzoate were charged to a vapor-liquid equilibrium still and refluxed for eleven hours. Analysis indicated a vapor composition of 46.1% p-menthane, 53.9% p-cymene; a liquid composition of 40% p-menthane, 60% p-cymene which is a relative volatility of 2.5.

EXAMPLE 4

Forty grams of a p-methane - p-cymene mixture and 20 grams of undecyl alcohol were charged to the vapor-liquid equilibrium still and refluxed for seven hours. Analysis indicated a vapor composition of 34.7% p-menthane, 65.3% p-cymene; a liquid composition of 60.9% p-menthane, 39.1% p-cymene which is a relative volatility of p-cymene to p-menthane of 2.9.

EXAMPLE 5

150 grams of a p-menthane - p-cymene mixture and 200 grams of isobutanol were charged to a glass perforated plate rectification column possessing 7.3 theoretical plates. After two hours at total reflux, overhead and bottoms samples were taken and analysed by gas chromatography. The overhead in the form of the p-menthane - isobutanol azeotrope, was 99.9% p-menthane, 0.1% p-cymene, the bottoms was 68.5% p-menthane, 31.5% p-cymene which is a relative volatility of 2.3. Refluxing gas continued for another two hours. Analysis indicated on overhead in the form of the p-menthane - isobutanol azeotrope of 99.9% p-menthane, 0.1% p-cymene; the bottoms was 58.5% p-menthane, 41.5% p-cymene which is a relative volatility of 2.4. This is data is presented in Table 7.

EXAMPLE 6

A solution comprising 400 grams of the p-menthane - p-cymene mixture was placed in the stillpot of the 7.3 theoretical perforated plate column. When refluxing began, an extractive agent comprising methyl benzoate was pumped into column at a rate of 15 ml/min. The temperature of the extractive agent as it entered the column was 95° C. After establishing the feed rate of the extractive agent, the heat input to the p-menthane - p-cymene in the stillpot was adjusted to give a total reflux rate of 40 ml/min. After one hour of operation, the overhead and bottoms samples of approximately two ml. were collected and analysed. The overhead analysis was 91% p-menthane, 9% p-cymene and the bottoms analysis was 21.2% p-menthane, 78.8% p-cymene. Using these compositions in the Fenske equation, with the number of theoretical plates in the column being 7.3, gave an average relative volatility of 1.64 for each theoretical plate. This data is presented in Table 7.

I claim:

1. A method for recovering p-menthane from a mixture of p-menthane and p-cymene which comprises distilling a mixture of p-menthane and p-cymene in the presence of about one part of an extractive agent per part of p-menthane - p-cymene mixture, recovering the p-menthane as overhead product and obtaining the p-cymene and the extractive agent from the stillpot, wherein said extractive agent comprises at least one material selected from the group consisting of methyl benzoate, ethyl benzoate, butyl benzoate, benzyl benzoate, benzyl acetate, methyl salicylate, diethyl maleate, ethylene glycol diacetate, acetophenone, 2-hydroxyacetophenone, benzyl ether, nonyl alcohol, diethylene glycol butyl ether, diethylene glycol hexyl ether and tripropylene glycol methyl ether.

2. A method for recovering p-cymene from a mixture of p-cymene and p-menthane which comprises distilling a mixture of p-cymene and p-menthane in the presence of about one part of an extractive agent per part of p-cymene - p-menthane mixture, recovering the p-cymene as overhead product and obtaining the p-menthane and the extractive agent from the stillpot, wherein said extractive agent comprises at least one material selected from the group consisting of isodecyl alcohol, undecyl alcohol, cyclododecanol, isobutyl heptyl ketone, 2-undecanone and glycerol triacetate.

* * * * *